United States Patent
Vogt et al.

(10) Patent No.: US 9,701,705 B2
(45) Date of Patent: Jul. 11, 2017

(54) METHOD FOR PRODUCING TRANSITION METAL COMPOUNDS, TRANSITION METAL COMPOUNDS AND USE THEREOF

(71) Applicant: Georg Vogt, Kempten (DE)

(72) Inventors: Georg Vogt, Kempten (DE); Henning Bock, Sonthofen (DE); Karl Thomas Fehr, Munich (DE)

(*) Notice: Subject to any disclaimer, the term of this patent is extended or adjusted under 35 U.S.C. 154(b) by 91 days.

(21) Appl. No.: 14/421,922

(22) PCT Filed: Aug. 16, 2013

(86) PCT No.: PCT/EP2013/067168
§ 371 (c)(1),
(2) Date: Jun. 26, 2015

(87) PCT Pub. No.: WO2014/027096
PCT Pub. Date: Feb. 20, 2014

(65) Prior Publication Data
US 2015/0307536 A1    Oct. 29, 2015

(30) Foreign Application Priority Data
Aug. 17, 2012 (DE) .................. 10 2012 016 486

(51) Int. Cl.
| | | |
|---|---|---|
| *C07F 15/04* | (2006.01) | |
| *C07F 15/02* | (2006.01) | |
| *C07F 13/00* | (2006.01) | |
| *C01B 21/06* | (2006.01) | |
| *C01B 21/082* | (2006.01) | |
| *C01B 31/30* | (2006.01) | |

(52) U.S. Cl.
CPC .......... *C07F 15/04* (2013.01); *C01B 21/0615* (2013.01); *C01B 21/0622* (2013.01); *C01B 21/0828* (2013.01); *C01B 31/303* (2013.01); *C07F 13/00* (2013.01); *C07F 15/02* (2013.01); *C01P 2002/50* (2013.01); *C01P 2002/72* (2013.01); *C01P 2002/76* (2013.01); *C01P 2002/77* (2013.01)

(58) Field of Classification Search
CPC .......... C07F 15/04; C07F 15/02; C07F 13/00; C01B 31/303; C01B 21/0828; C01B 21/0622; C01B 21/0615
USPC ....................................................... 544/181
See application file for complete search history.

(56) References Cited

U.S. PATENT DOCUMENTS 1,772,107 A    8/1930    Nelson

FOREIGN PATENT DOCUMENTS

| DE | 19634777 A1 | 3/1998 |
|---|---|---|
| DE | 102008045742 A1 | 3/2010 |
| DE | 102009034090 A1 | 1/2011 |
| GB | 2232991 A | 1/1991 |
| KR | 100957128 B1 | 5/2010 |
| RU | 1772107 A1 | 10/1992 |

OTHER PUBLICATIONS

T. Komatsu; "Attempted Chemical Synthesis of Graphite-like Carbon Nitride"; The Royal Society of Chemistry 2001; J. Mater. Chem., 2001.11.799 801; Feb. 5, 2001; pp. 799-801.
Xingcai Wu et al.; "High-pressure pyrolysis of melamine route to nitrogen-doped conical hollow and bamboo-like carbon nanotubes"; Key Laboratory of Mesascopic Chemistry, Nanjing University; Oct. 17, 2005; pp. 164-170.
B. V. Lotsch; "From molecular building blocks to condensed carbon nitride networks: structure and reactivity"; Fakultat fur Chemie and Pharmazie der Ludwig-Maximilans-Universitat Munchen; Nov. 20, 2006; pp. 246-262.
Xinchen Wang et al.; "Metal-containing carbon nitride compounds: a new functional organic-metal hybrid material"; Advanced Materials Communication; 2009, 21, pp. 1609-1612.
Zhengxin Ding et al.; "Synthesis of transition metal-modified carbon nitride polymers for selective hydrocarbon oxidation"; ChemsusChem; D01:10.1002/cssc.201000149; 2011; pp. 274-281.
Cun Li et al.; "Synthesis and characterization of nitrogen-rich graphitic carbon nitride"; Materials Chemistry and Physics 103; 2007; pp. 427-432.
M. Lei et al.; "Synthesis aof transition metal carbide nanoparticles through melamine and metal oxides"; MElsevier; 2008; pp. 1671-1677.

*Primary Examiner* — Porfirio Nazario Gonzalez
(74) *Attorney, Agent, or Firm* — Miles & Stockbridge PC

(57) ABSTRACT

The invention relates to a method for producing transition metal compounds having the general composition $Me_aC_bN_cH_d$ where Me=transition metal or transition metal mixture, a=1-4, b=6-9, c=8-14 and d=0-8, wherein a reaction mixture consisting of transition metals and/or transition metal compounds and non-condensed or slightly condensed C—N—H compounds are subjected to a heat treatment, wherein the content of transition metals and/or transition metal compounds is at least 6 mole percent, preferably 10 to 40 mole percent, relative to the reaction mixture. The invention further relates to transition metal compounds produced in such a manner and to uses thereof.

33 Claims, No Drawings

METHOD FOR PRODUCING TRANSITION METAL COMPOUNDS, TRANSITION METAL COMPOUNDS AND USE THEREOF

The present invention relates to a method for producing transition metal compounds of the general composition of $Me_aC_bN_cH_d$, wherein Me=transition metal or transition metal mixture, a=1-4, b=6-9, c=8-14, d=0-8, wherein a reaction mixture consisting of transition metals and/or transition metal compounds and non-condensed or slightly condensed C—N—H compounds is subjected to a heat treatment. Furthermore, the invention relates to correspondingly produced transition metal compounds and the use thereof.

The present invention is to be associated with the material system of carbon, nitrogen, hydrogen and transition metal with respect to the input materials as well as the reaction conditions. In a plurality of operations, the material system C, N, H is reported. Examinations in the material system C, N, H, transition metal focus on the production of nitrides and carbides of some transition metals as well as on the synthesis of incorporation compounds, in which the transition metal is in a graphitic carbon nitride structure constructed of planar s-triazine units. Many methods known from the prior art for producing carbon nitrides involve pyrolysis of chemical substances and/or substance mixtures. DING, Z. (among others) report the production of graphitic carbon nitride constructed of planar s-triazine units with transition metals (Cu, Ni, Mn, Fe, Co) incorporated in the lattice of the graphitic carbon nitride in ChemSusChem, Vol. 4, 2011, p. 274-281: "Synthesis of Transition Metal-Modified Carbon Nitride Polymers for Selective Hydrocarbon Oxidation". Ding, Z. (among others) obtained "Transition Metal-Modified Carbon Nitride Polymers" by heat treatments of reaction mixtures of the molar composition of 94.7% of dicyandiamide and 5.3% of metal chloride at 500-600° C. and a duration of 4 hours. Reaction products were obtained, in which the metal is embedded in a graphitic lattice of polymer heptazine rings. The X-ray powder diagram of these materials shows Bragg reflections with d-values of: 3.230+_0.020. However, this known prior art is disadvantageous in that the graphitic structures exclusively obtained by the heat treatment have undesired and economically non-interesting physical characteristics.

Therefore, the present invention is based on the object to provide a method for producing transition metal compounds of the initially mentioned kind, which allows the inexpensive production of a starting material for producing economically interesting valuable materials, in particular valuable materials containing carbon and nitrogen having cubic phases. Further, it is the object of the present invention to provide a correspondingly produced transition metal compound.

This object is satisfied by a generic method having the features of claim 1, a thus produced transition metal compound having the features of claim 14, a transition metal compound having the features of claim 16 and uses of this transition metal compound according to the invention having the features of claims 18 and 19. Advantageous configurations with convenient developments of the invention are specified in the respective dependent claims, wherein advantageous configurations of the method are to be considered as advantageous configurations of the transition metal compounds. Conversely, advantageous configurations of the transition metal compounds are also to be considered as advantageous configurations of the method.

In the conversion of non-condensed or slightly condensed C—N—H compounds with transition metals and/or transition metal compounds, it was surprisingly determined that completely different reaction products are obtained depending on the employed amount of metal. The invention is based on the realization that in heat treatment in a first temperature range between 150° C. and 570° C., in particular between 300° C. and 540° C., of reaction mixtures consisting of non-condensed or only slightly condensed C—N—H compounds such as for example cyanamide, dicyandiamide or melamine and an amount of transition metal and/or transition metal compounds sufficient for formation of clusters, wherein the content of transition metals and/or transition metal compounds is at least 6 mole percent, preferably 10 to 40 mole percent, related to the reaction mixture, compounds of the general composition of $Me_aC_bN_cH_d$, wherein Me=transition metal or transition metal mixture, a=1-4, b=6-9, c=8-14, d=0-8 are formed, in which $C_6N_9H_4$ units directly or indirectly bound to the transition metal are present. In particular, proportions of 6 mole %, 7 mole %, 8 mole %, 9 mole %, 10 mole %, 11 mole %, 12 mole %, 13 mole %, 14 mole %, 15 mole %, 16 mole %, 17 mole %, 18 mole %, 19 mole %, 20 mole %, 21 mole %, 22 mole %, 23 mole %, 24 mole %, 25 mole %, 26 mole %, 27 mole %, 28 mole %, 29 mole %, 30 mole %, 31 mole %, 32 mole %, 33 mole %, 34 mole %, 35 mole %, 36 mole %, 37 mole %, 38 mole %, 39 mole % or 40 mole % as well as corresponding intermediate values such as for instance 29.0 mole %, 29.1 mole %, 29.2 mole %, 29.3 mole %, 29.4 mole %, 29.5 mole %, 29.6 mole %, 29.7 mole %, 29.8 mole %, 29.9 mole % etc. are to be understood by a content of transition metals and/or transition metal compounds. In particular, temperatures of 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., 350° C., 360° C., 370° C., 380° C., 390° C., 400° C., 410° C., 420° C., 430° C., 440° C., 450° C., 460° C., 470° C., 480° C., 490° C., 500° C., 510° C., 520° C., 530° C., 540° C., 550° C., 560° C., 570° C. as well as corresponding intermediate values such as for instance 305° C., 315° C., 325° C., 335° C., 345° C. or 535° C. and 545° C. are to be understood by a first temperature range between 150° C. and 570° C.

Transition metal compounds produced according to the method according to the invention contain di-imino-tri-s-triazine as a component. Only with the mentioned high proportion of transition metal in the reaction mixture, the formation of metal clusters is allowed, the supply of delocalized electrons of which in the condensation of the non-condensed or only slightly condensed C—N—H compounds such as for example melamine or dicyandiamide or cyanamide entails the formation and stabilization of compounds, in which di-imino-tri-s-triazine tautomers exist bound to transition metals. The formation of graphitic structures in the use of the transition metal compounds according to the invention is reliably prevented. Thereby, the transition metal compounds according to the invention can serve for producing economically interesting valuable materials, in particular valuable materials containing carbon and nitrogen, having cubic phases. The transition metal compounds according to the invention have a metal carbide structure, for example an X-ray diffractogram comparable to the nickel carbide for example in using nickel. They are only obtained in the conversion of reaction mixtures with high transition metal contents, i.e. at least 6 mole percent, preferably 10 to 40 mole percent, related to the reaction mixture. The Bragg reflections of the X-ray powder diagrams of the transition metal compounds according to the invention prove the presence of materials present in a crystal lattice analogous to the metal carbide, for example the nickel carbide. It can be inferred from the thermal behavior of these materials that—with use of nickel as the transition metal—nickel carbide $Ni_3C$ is not present. The molar ratio of transition metal and/or transition metal compound to the slightly condensed C—N—H compounds is advantageously each between 1:2 and 1:8.

In advantageous configurations of the method according to the invention, the heat treatment can be performed in one-stage or multi-stage manner or in alternating manner within the first temperature range. Furthermore, there is the possibility that the heat treatment is performed within the first temperature range over a period of time between 5 minutes and 500 hours in continuous manner or in time intervals. In particular, periods of time of 5 min, 10 min, 15 min, 20 min, 25 min, 30 min, 35 min, 40 min, 45 min, 50 min, 55 min, 60 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 25 h, 26 h, 27 h, 28 h, 29 h, 30 h, 31 h, 32 h, 33 h, 34 h, 35 h, 36 h, 37 h, 38 h, 39 h, 40 h, 41 h, 42 h, 43 h, 44 h, 45 h, 46 h, 47 h, 48 h, 50 h, 100 h, 150 h, 200 h, 250 h, 300 h, 350 h, 400 h, 450 h, 500 h as well as corresponding intermediate values such as for instance 8 min, 12 min, 22 min, 1.5 h, 2.5 h, 3.5 h, 4.5 h, 5.5 h, 6.5 h, 7.5 h, 8.5 h, 9.5 h or 48.5 h, 50.5 h, 75.5 h, 85.5 h, 100.5 h or 255 h are to be understood by a period of time between 5 minutes and 500 hours.

In further advantageous configurations of the method according to the invention, the transition metals and/or transition metal compounds are selected from the group of the transition metals acting as catalysts or from the group of the elements forming carbonyl complexes. Transition metal compounds according to the invention are in particular also obtained if transition metals forming carbonyl complexes and/or suitable as hydrogenating catalysts such as manganese, iron, cobalt, nickel, platinum are used individually or in mixture in the reaction mixture. As the transition metals, for example, nickel and/or cobalt and/or manganese and/or iron and/or platinum and/or niobium and/or iron and/or tungsten and/or tantalum and/or copper and/or zinc can be employed. Preferably, the transition metals are employed in elemental form as a powder.

In further advantageous configurations of the method according to the invention, preferably, cyanamide and/or ammonium dicyandiamide and/or dicyandiamide and/or melamine are employed as the slightly condensed C—N—H compounds. In particular compounds are understood by non-condensed or slightly condensed C—N—H compounds, which result in precursors of the carbon nitride like melem in further condensation.

In further advantageous configurations of the method according to the invention, cyanides and/or cyano complexes and/or isocyan complexes, in particular those having a cubic lattice structure, are added to the reaction mixture according to the invention consisting of non-condensed or slightly condensed C—N—H compounds and transition metals and/or transition metal compounds.

In a further advantageous configuration of the method according to the invention, boron powders and/or boron compounds such as for example lithium boride $LiB_{12}$ and/or other nitride forming elements and/or the compounds thereof are added to the reaction mixture according to the invention consisting of non-condensed or slightly condensed C—N—H compounds and transition metals and/or transition metal compounds before and/or after one or more heat treatments in the first temperature range.

In advantageous configurations of the method according to the invention, after the heat treatment in the first temperature range between 150° C. and 570° C., at least one further heat treatment in a second temperature range between 520° C. and 700° C. is effected. In particular, temperatures of 520° C., 530° C., 540° C., 550° C., 560° C., 570° C., 580° C., 590° C., 600° C., 610° C., 620° C., 630° C., 640° C., 650° C., 660° C., 670° C., 680° C., 690° C., 700° C. as well as corresponding intermediate values such as for instance 545° C., 555° C., 565° C., 575° C., 585° C. or 635° C. and 645° C., are to be understood by a second temperature range between 520° C. and 700° C. In this thermolysis of the transition metal compounds according to the invention, the imino groups become available as a part of isocyan components for the formation of stable transition metal complexes. The characteristic of the transition metal compounds according to the invention to form materials with cubic lattice structure in the thermolysis is due to the presence of isocyan structures in the di-imino-tri-s-triazine molecule. While for example melem is converted to a C—N material similar to graphite at temperatures above 560° C., the di-imino-tri-s-triazine transition metal compounds according to the invention have the excellent characteristic of converting themselves to material containing carbon and nitrogen with cubic lattice structure in the thermolysis. From the prior art, it is not known that by heat treatment of reaction mixtures consisting of for example cyanamide and/or dicyandiamide and/or melamine and one and/or more transition metals, reaction products are obtained, in which a C—N—H transition metal compound is present, which forms a material containing carbon, nitrogen and hydrogen, having cubic phases in further heat treatment. Further, it is not known from the prior art that such materials having cubic phases are used for producing carbides and/or nitrides present in the cubic lattice. The use of the compounds according to the invention as a starting material for producing materials containing carbon and/or nitrogen, present in cubic lattice structure is therefore also a subject matter of the invention. In the heat treatment of a compound according to the invention at temperatures greater than 520° C., carbon present in cubic lattice structure is obtained as the thermolysis product. If the X-ray diffractograms of thermolysis products show the Bragg reflections of cubic carbon, thus, there is the evidence that a compound according to the invention has been subjected to the thermolysis. The production of materials containing carbon and/or nitrogen, present in the cubic crystal lattice under mild reaction conditions does not only present the technically and economically better solution for those materials, the production of which according to the prior art is only possible under expensive technical conditions—such as high pressures and temperatures—but also exploits possibilities of the development of new materials. It was not to be expected by the man skilled in the art that with high transition metal contents in a reaction mixture consisting of non-condensed or slightly condensed C—N—H compounds and transition metal, transition metal compounds having cubic phases in the C—N—H material system are obtained. These compounds can—analogously to the compounds containing transition metal in the graphitic carbon nitride, Me-g-C3N4—be considered as compounds containing transition metal in the cubic carbon nitride, Me-c-C3N4. In the heat treatment of the transition metal compound according to the invention in the second temperature range between 520° C. and 700° C., for example, nickel transport in the gaseous phase can be observed. This observation allows the conclusion that in the heat treatment according to the invention of the transition metal compounds according to the invention, tetragonal tetraisocyan transition metal (0) complexes analogous to the tetragonal nickel (0) tetracarbonyl complex are formed, which come into consideration in situ for the formation of the materials present in the cubic crystal lattice. The use of tetragonal isocyan transition metal (0) complexes having cubic phases as reactive templates for producing materials containing cubic carbide and/or nitride and/or carbonitride phases is also the subject matter of the invention. Transition metal compounds according to the invention having for example a crystal lattice analogous to the nickel carbide and subjected to the mentioned further heat treatment in the second temperature range, surprisingly transition to reaction products, which show Bragg reflections in the X-ray powder diagram, according to which materials are present in a cubic space group similar to the diamond. Therein, for example the following d-values have been determined: 2.045v, 1.774s, fluctuation range: ±0.01 (for comparison: cubic carbon d-values: 2.043vs, 1.769w, 1.251s).

In addition, for example after addition of boron powder and/or boron compounds such as for example lithium boride LiB12 and/or other nitride forming elements and/or the compounds thereof, the further heat treatment in the second temperature range can be performed. Cubic boron nitride is formed from the reaction mixtures consisting of the transition metal compounds according to the invention and boron powder and/or boron compounds at heat treatment temperatures above 500° C. If Bragg reflections associated with the cubic boron nitride are found in the X-ray diffractogram of the reaction products from such heat treatments, thus, these Bragg reflections are an evidence of the presence of transition metal compounds according to the invention in the reaction mixture used for thermolysis.

In advantageous configurations of the method according to the invention, the second heat treatment can also be performed in one-stage or multi-stage manner or in alternating manner within the second temperature range. There is also the possibility that the second heat treatment is performed such that it encompasses the first and the second temperature range. Furthermore, there is the possibility that the heat treatment within the second temperature range is performed over a period of time between 5 minutes and 500 hours in continuous manner or in time intervals. In particular, periods of time of 5 min, 10 min, 15 min, 20 min, 25 min, 30 min, 35 min, 40 min, 45 min, 50 min, 55 min, 60 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 25 h, 26 h, 27 h, 28 h, 29 h, 30 h, 31 h, 32 h, 33 h, 34 h, 35 h, 36 h, 37 h, 38 h, 39 h, 40 h, 41 h, 42 h, 43 h, 44 h, 45 h, 46 h, 47 h, 48 h, 50 h, 100 h, 150 h, 200 h, 250 h, 300 h, 350 h, 400 h, 450 h, 500 h as well as corresponding intermediate values such as for instance 8 min, 12 min, 22 min, 1.5 h, 2.5 h, 3.5 h, 4.5 h, 5.5 h, 6.5 h, 7.5 h, 8.5 h, 9.5 h or 48.5 h, 50.5 h, 75.5 h, 85.5 h, 100.5 h or 255 h are to be understood by a period of time between 5 minutes and 500 hours.

Furthermore, the invention relates to transition metal compounds of the general composition of $Me_aC_bN_cH_d$, wherein Me=transition metal or transition metal mixture, a=1-4, b=6-9, c=8-14, d=0-8 produced according to a method as described above within the scope of a heat treatment in the first temperature range. Therein, these transition metal compounds advantageously have a metal carbide structure.

Furthermore, the invention relates to transition metal compounds of the general composition of $Me_aC_bN_cH_d$, wherein Me=transition metal or transition metal mixture, a=1-4, b=6-9, c=8-14, d=0-8 wherein the transition metal compound has at least one $C_6N_9H_4$ unit directly or indirectly bound to the transition metal or the transition metal mixture, which is present as di-imino-tri-s-triazine. The transition metal compounds contain di-imino-tri-s-triazine as a component. Only with the mentioned high proportion of transition metal in the reaction mixture, the formation of metal clusters is allowed, the supply of delocalized electrons of which entails the formation and stabilization of compounds in the condensation of the non-condensed or only slightly condensed C—N—H compounds such as for example melamine or dicyandiamide or cyanamide, in which di-imino-tri-s-triazine tautomers exist bound to transition metals. The formation of graphitic structures in the use of the transition metal compounds according to the invention is reliably prevented. Thereby, the transition metal compounds according to the invention can serve for the production of economically interesting valuable materials, in particular valuable materials containing carbon and nitrogen, having cubic phases. The transition metal compounds according to the invention have an X-ray diffractogram comparable to the transition metal carbide. The transition metal compounds according to the invention can for example have the following structural formulas: $Me_3C_2HN(C_6N_9H_4)$, $Me_6C_4H_2(C_6N_9H_4)_2$ or $Me_3(C_6N_9H_4)_3$. Therein, the transition metal compounds advantageously have a metal carbide structure.

According to the invention, the transition metal compounds produced according to a method described above within the scope of a heat treatment in the first temperature range are used for producing materials containing carbon and/or nitrogen, present in the cubic crystal lattice.

The use of tetragonal isocyan transition metal (0) complexes for producing materials containing carbon and/or nitrogen, present in the cubic crystal lattice is also encompassed according to the invention. The transition metal compounds according to the invention and tetragonal tetraisocyan transition metal (0) compounds are usable as reactive templates for producing materials containing cubic carbide, nitride and/or carbonitride. An addition of compounds containing CN groups, such as for example cyanides and/or cyano complexes present in cubic lattice structure, to the reaction mixture according to the invention extends the possibilities of use of such reaction mixtures as reactive templates.

The present invention provides access as simple as possible to the materials according to the invention. A crucial feature of the method according to the invention is the selection of the transition metals. The transition metals are for example selected from the group of the transition metals forming carbonyls. A further feature of the method according to the invention is the composition of the reaction mixture. The molar proportion of transition metal in the reaction mixture is at least 6 percent. Preferably, reaction mixtures with a molar proportion of transition metal between 10 and 40 percent are employed. The reaction mixture can be subjected to the heat treatment as bulk material. With occurring melting phases, by suitable measures as shaking or stirring, demixing of the reaction partners is to be prevented. The heat treatment can be performed in one or more stages. With a multi-stage heat treatment, after each treatment stage, crushing and homogenization of the obtained reaction product can be performed. The multi-stage heat treatment can additionally be composed of a pretreatment and one and/or more main treatments. The pretreatment in particular includes heating the reaction mixture to one and/or more pretreatment temperatures, dwelling at these pretreatment temperatures, cooling down, crushing and homogenizing the obtained pretreatment product. The pretreatment temperatures are preferably in the range between 150° C. and 400° C. In particular, temperatures of 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., 350° C., 360° C., 370° C., 380° C., 390° C., 400° C. as well as corresponding intermediate values such as for instance 245° C., 255° C., 265° C., 275° C., 285° C., 335° C. or 345° C. are to be understood by pretreatment temperatures. In this temperature range, melting phases can basically occur, to which—depending on the composition of the reaction mixture—conversion reactions associated with severe gas emission can follow. The duration of dwelling is basically a non-crucial parameter. A dwelling time in the pretreatment between 10 min and a few hours is usual. In particular, periods of time of 10 min, 15 min, 20 min, 25 min, 30 min, 35 min, 40 min, 45 min, 50 min, 55 min, 60 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h as well as corresponding intermediate values such as for instance 1.5 h, 2.5 h, 3.5 h are to be understood by a period of time between 10 min and a few hours. After the pretreatment, a product is present, in which the transition metal can be present in a partially reacted form. The main treatment then includes heating the crushed and homogenized product obtained in the pretreatment and/or heating the starting reaction mixture to one and/or more main treatment temperatures, namely the first and/or the second temperature ranges, dwelling at these temperatures, cooling down to room temperature, crushing and homogenizing. The temperatures applied in the first heat treatment for producing the transition metal compound according to the invention are in the first temperature range between 150° C. and 570° C., in particular between 300° C. and 540° C. or between 400° C. and 550° C. With the second heat treatment of the transition metal compound according to the invention, the obtained, crushed and homogenized transition metal compound according to the invention is subjected to a second temperature range between 520° C. and 700° C., preferably between 550° C. and 590° C. The dwelling time is between a few minutes and several hours. Therein, a material is obtained, which has Bragg reflections similar to the cubic carbon in the X-ray powder diagram. If an element forming nitride and/or carbide, for example elemental boron and/or a boron compound, is admixed to the transition metal compound according to the invention and/or the material obtained by the second heat treatment, the mixture is homogenized and is subjected to a further heat treatment in the temperature range from 500° C. to 700° C., in particular between 550° C. and 620° C.—at a dwelling time between a few minutes and several hours—then, a further reaction product is obtained, which has Bragg reflections for example similar to the cubic boron nitride in the X-ray powder diagram.

Heat treatments of reaction mixtures containing C—N—H compounds and transition metals can be performed in normal containers of metal, glass or quartz glass suitable for the reaction. Volatile by-products arising in the heat treatment can preferably be separated in and/or after each treatment step, for example by escaping, by diffusing or absorbing. The heat treatment can be performed at negative pressure and/or normal pressure and/or at moderate overpressure and/or at high pressures generated by applying external pressure. The heat treatment can be performed with or without protective gas. Reaction products obtained from the heat treatment are preferably present as reproducible solids.

Examinations and considerations give reason to expect that new materials can be accessible with the aid of the materials according to the invention containing carbon and nitrogen, having cubic phases. The compounds and materials producible according to the method according to the invention can have further characteristics, which make their use advantageous in the most different fields, e.g. as catalysts in organic reactions, as solid electrolytes, as energy storages, sensors, semiconductors, fillers, grinding and polishing agents, ceramic and cermets. The characteristics of the materials according to the invention can be altered if further elements and/or their compounds, for example carbides, nitrides, borides, cyanides and/or cyano complexes, are added to the reaction mixture. The production and use of such metal containing materials in particular containing carbon and nitrogen, having cubic phases, which contain further elements, is also the subject matter of the present invention.

Further features of the invention are apparent from the depictions as well as from the following examples. Herein, the individual features can be realized each separately or in multiple in combination with each other in an embodiment of the invention. The following examples prove the invention, but do not restrict it in its width. Furthermore, the following examples prove the employment of various transition metals and transition metal compounds as well as also the use of the compounds according to the invention in the reaction system hydrocarbons—ammonia. Depending on the reaction parameters of metal concentration in the reaction mixture, heating speed, gas pressure, temperature and duration of the heat treatment, various structural types of the compounds according to the invention are obtained.

EXAMPLE 1

Heat treatment of a reaction mixture in the molar ratio of nickel to dicyandiamide=1:4.2 for producing a transition metal compound.

From nickel powder and dicyandiamide in the molar mixture ratio of 1:4.2, a homogenous mixture was produced by intensively mixing. 2.5 g of this reaction mixture was placed in a glass reactor provided with a pressure regulating device. First, the mixture was heated up to the beginning melting of the dicyandiamide and kept at this temperature (ca. 205° C.) for ca. 2 minutes. During this phase, the reactor was shaken to avoid demixing by settling of the nickel particles. After onset of the severely exothermic decomposition reaction of the dicyandiamide identifiable by a gas surge and simultaneous temperature rise of the reaction item to ca. 360° C., pressure equalization was performed. In the subsequent heat treatment, the present reaction mixture was heated up to 520° C. in the course of 30 minutes and subsequently kept at a temperature between 520 and 530° C. for the duration of 20 minutes. After cooling down to room temperature and evacuating the reactor, an olive-brown powder was obtained as the reaction product, characterized by the following d-values of the Bragg reflections: 3.253w, 2.933w, 2.294s, 2.172s, 2.029vs, 1.577s (the suffixes to the d-values signify: w=weak, s=strong, vs=very strong).

The powder obtained as the reaction product was subjected to elemental analysis without further conditioning. C—N—H—O combustion analysis provided the following values in percent by weight: carbon 22.9, nitrogen 34.07, hydrogen 1.16, oxygen 1.68 and nickel 40.19 (from difference to 100). From the values of the elemental analysis, the following stoichiometric composition of the reaction product is computationally obtained: $Ni_3C_8H_{10}N_5$. In the production of the reaction product described in example 1, a part of the heat treatment was performed under NH3 pressure. With the chemical formula of Ni3C8N10H5, a compound is present, in which a (C6N9H4) residue is linked to a Me3 cluster via —N=CH—C. The compound has the structure: Ni3C2HN(C6N9H4) and can be represented as follows:

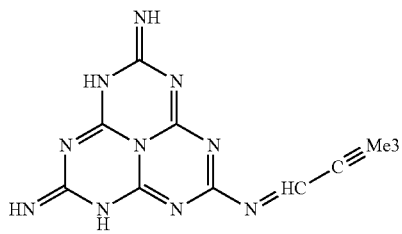

EXAMPLE 2

Heat treatment of a reaction mixture in the molar ratio of nickel to dicyandiamide=1:2.15 for producing a transition metal compound.

A reaction mixture of nickel powder and dicyandiamide in the molar ratio of 1:2.15 was produced. The reaction mixture was filled into a glass reactor. The reactor was evacuated, the reaction mixture was heated to ca. 200-230° C., melting phase, shaking, low gas surge. Then, the reaction mixture was heated up to 520° C. during 20 minutes and kept at this temperature for 40 minutes. After cooling down, a brown reaction product was obtained. After crushing and homogenizing, the reaction product was subjected to elemental analysis without further conditioning. C—N—H—O combustion analysis provided the following values in percent by weight: carbon 22.6, nitrogen 29.8, hydrogen 1.14, oxygen 1.85 and nickel 44.61 (from difference to 100% by wt.). The reaction product has the following d-values: 2.29s, 2.17s, 2.0289vs, 1.57s. From the values of the elemental analysis, the following stoichiometric composition of the reaction product is computationally obtained: Ni3C8N9H5. A dimeric compound is present: (C6N9H4)-CH=C=Me2-Me-Me-Me2=C=HC—(C6N9H4). The corresponding chemical formula Ni6C4H2(C6N9H4)2 can be represented as follows (wherein Me=Ni):

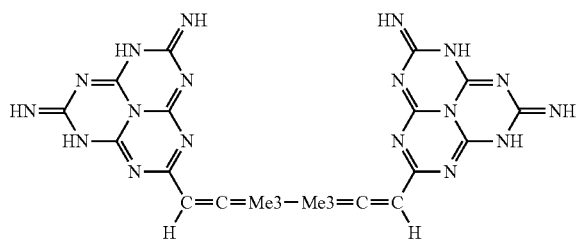

EXAMPLE 3

With a reaction mixture consisting of dicyandiamide and nickel powder in the molar mixture ratio of 4.5:1, according to the method described in example 1, a transition metal compound was produced at a first heat treatment temperature of 400° C. and a treatment duration of 100 minutes. 0.5 g of this reaction product were placed in a glass reactor, the filled reactor was provided with an open capillary and introduced into a tube furnace. The reaction product thus introduced into the tube furnace was subjected to a second heat treatment temperature of 570° C.-580° C. with a dwelling time of 30 minutes. After cooling down, a grey-brown powder was obtained as the reaction product. The d-vales obtained by X-ray diffraction with a powder diffractometer of 2.054vs and 1.780s are very similar to the d-values of 2.043 and 1.769 known for the cubic carbon phase.

EXAMPLE 4

A reaction mixture consisting of dicyandiamide, nickel powder and manganese powder in the molar ratio of 8:1:1 was treated according to the method described in example 1. Heat treatment temperature: 500° C., dwelling time: 60 minutes. First reaction product: grey powder with the following d-values: 2.300s, 2.158s, 2.033vs, 1.577s. 0.7 g of the homogenized reaction product/powder was subsequently intensively mixed with 0.15 g of amorphous boron powder and this mixture was introduced into a quartz glass reactor. The filled reactor equipped with a pressure regulating assembly was placed in a treatment furnace and subjected to a further heat treatment at a temperature of 580° C. with a dwelling time of 4.5 hours. As a further reaction product, a brown powder was obtained, characterized by the following d-values of the Bragg reflections: d-values: 2.089vs, 1.791s, 1.765w.

The found d-values of 2.089vs and 1.791s are in the range of the Bragg reflections known for cubic boron nitride with the d-values of 2.078vs and 1.804s. As a further (final) reaction product, a compound containing nickel, manganese, carbon, nitrogen, hydrogen and boron is present. This observation reveals that the cubic carbon phases arising in the further heat treatment of transition metal compounds act in situ as reactive templates in the presence of boron in the reaction mixture with formation of compounds present in the cubic boron nitride crystal lattice. This proves the existence of a material containing carbon and nitrogen present in the cubic lattice, which is capable of passing the cubic structure in the formation of a nitride.

For the first reaction product described in example 4 of dicyandiamide, nickel powder and manganese powder in the molar ratio of 8:1:1 at 500° C. and 60 minutes of dwelling time with the d-values of 2.30s, 2.158s, 2.033vs, 1.57s, the following values were obtained in an elemental analysis: C, 27.85% by wt., H, 1.58% by wt., N, 48.67% by wt., Ni/Mn=21.9% by wt. (difference to 100% by wt.) Chemical formula: MeC6N9H4(Me=(Ni/Mn)). The structural formula Me3(C6N9H4)3 can be represented as follows (wherein Me=(Ni/Mn)):

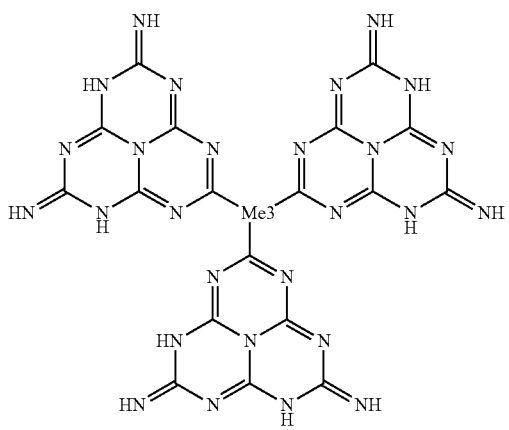

A further reaction mixture as in example 4, only with nickel powder, molar ratio dicyandiamide:nickel=4:1, same experimental parameters, resulted in a reaction product with the d-values: 3.26s, 2.29s, 2.17s, 2.028vs, 1.57s and the following values of the chemical elemental analysis: C, 28.44%, H, 1.68%, N, 47.93%, difference to 100=metal. Chemical formula NiC6N9H4; structural formula: Ni3(C6N9H4)3 (see also example 4; Me=Ni).

In the heat treatment of a reaction mixture corresponding to the prior art, consisting of dicyandiamide and 5.4 mole % of nickel, treatment duration 50 h at a temperature of 570° C., a compound with the composition of Ni(C6N9H4)3 was obtained, characterized by a d-value of 3.23. In this thermolysis product, the metal is embedded in a graphitic lattice of polymeric heptazine rings. In the thermolysis of the transition metal compounds according to the invention such as for example Ni3(C6N9H4)3, in contrast, carbon present in the cubic crystal lattice is obtained, characterized by the d-values of 2.054vs, 1.77s and 1.25. The conspicuous differences of the characteristics of the two compounds can be plausibly explained in that the C6N9H4 molecules are present in two tautomeric forms. In Ni(C6N9H4)3, the C6N9H4 is present as di-amino-tri-s-triazine, in contrast, in Ni3(C6N9H4)3 as di-imino-tri-s-triazine. The formation of stable di-imino-tri-s-triazine tautomers in the heat treatment of reaction mixtures consisting of dicyandiamide or similar slightly condensed C—N—H compounds and high proportions of transition metal is due to the presence of metal clusters and the thereby present supply of delocalized electrons.

In the above mentioned compounds of Ni3C8N10H5 (example 1) and Ni3C8N9H5 (example 2), the di-imino-tri-s-triazine components can be recognized in the described structural formulas. If one considers the di-imino-tri-s-triazine molecule, thus, one recognizes that the imino groups are present as isocyan hydrogen components bound to nitrogen. These components result in the formation of transition metal isocyan complexes in the thermolysis of transition metal di-imino-tri-s-triazine compounds.

EXAMPLE 5

By intensively mixing, a reaction mixture consisting of cyanamide, nickel powder, manganese powder, zinc cyanide powder and boron powder in the molar ratio of 2.8:1:1:1:6.3 was produced. 2.6 g of this mixture was filled into a nickel tube (internal diameter 6.0 mm), the tube was closed on both sides and introduced into a container with internal diameter of 12 mm. The space between container and tube was filled up with melamine, the container was closed and placed in a chamber furnace. After a first heat treatment over 90 minutes at 540-560° C., a modified main treatment with a duration of 4 days was effected, wherein the furnace was kept at the following temperatures alternately of each 12 hours: 590, 540, 600, 560, 610, 540, 620, then 6 hours 630 and 9 hours 660° C. As the reaction product, 1.8 g of a black-brown powder was obtained, characterized by the following d-values of the Bragg reflections: 4.757s, 2.691s, 2.116vvs, 2.0351w, 1.835vs, 1.675s, 1.297s and 1.107s.

The found d-values of 2.116vvs and 1.835vs and 1.297s show similarity with the Bragg reflections existing for cubic boron nitride of the X-ray powder diagram. The distance of the two reflections of 2.116 and 1.835 is 0.281, with c-BN, this value is at 0.274. The temperature resistance—9 hours at 660° C.—can be assessed as a further indication of the presence of a material containing cubic boron nitride.

EXAMPLE 6

Production of a transition metal compound of the composition of MeC6N9H4 wherein Me=Ni.

From 0.7 g nickel powder and 4.3 g dicyandiamide, a homogenous mixture was produced by intensively mixing. The entire amount of the reaction mixture was heated in an open quartz test tube above a flame up to beginning exothermic decomposition reaction of the dicyandiamide. Then, the test tube was closed and placed in a chamber furnace preheated to ca. 540° C. After 45 minutes, the test tube was removed at a temperature of 535° C. 3.2 g of light brown, non-magnetic reaction product was obtained. The results of the elemental analysis of the homogenized product in percent by weight: C, 28.44, N, 47.93, H, 1.68 and nickel from difference to 100:21.95. The product shows the following Bragg reflections: 3.244s, 2.292s, 2.170s, 2.027vs, 1.577s, 1.224s (see figure 1).

The reaction product described in example 6 was obtained by heat treatment of a reaction mixture at atmospheric pressure. The elemental analysis yielded the chemical formula NiC6N9H4. The compound has a lattice analogous to the nickel carbide Ni3C, wherefore this compound is present in the structure of Ni3(C6N9H4)3. The corresponding structural formula Ni3(C6N9H4)3 can be taken from example 4. In this compound with trimeric structure, each one Ni atom of the Ni3 cluster is linked to each one di-imino-tri-s-triazine.

EXAMPLE 7

Production of a reaction product containing carbon present in the cubic crystal lattice.

The production of this reaction product is identical with the approach described in example 6 concerning the reaction mixture, input amount and course of the procedure including the stage of the exothermic decomposition of dicyandiamide. After the test tube was closed, it was placed in a chamber furnace preheated to ca. 560° C. After 45 minutes, the test tube was removed at a temperature of 555° C. 2.4 g of a brown-grey magnetic reaction product was obtained. The results of the elemental analysis of the homogenized product in percent by weight: C, 28.68, N, 43.10, H, 1.50, nickel from difference to 100:26.72. The product shows the following Bragg reflections: 3.236s, 2.289w, 2.169w, 2.052vs, 2.025s, 1.776s, 1.256s (see figure 2).

EXAMPLE 8

Production of a transition metal compound of the composition of MeC6N9H4, wherein Me=0.5 Ni/0.5 Mn.

The production of this transition metal compound is described in example 4. It is the first reaction product described there, in which dicyandiamide, nickel powder and manganese powder were converted in the molar ratio of 8:1:1 at 500° C. and a dwelling time of 60 minutes. The elemental analysis of the obtained grey reaction product yielded the following values in percent by weight: C, 27.85, N, 48.67, H, 1.58, Ni/Mn=21.9. Structure: Me3(C6N9H4)3 Me=Ni/Mn (see also example 4).

The further processing of this transition metal compound with an addition of boron powder to a reaction product containing cubic boron nitride is described in example 4.

EXAMPLE 9

Use of the transition metal compound described in example 8 of the general composition of MeC6N9H4 wherein Me=0.5 Ni/0.5 Mn for the production of carbon present in the cubic crystal lattice.

The reaction product described in example 8 was placed about 10 mm high on the bottom of a quartz glass reactor disposed perpendicularly. A nickel tube immersing ca. 5 mm in this bulk was approximately centrally fixed in the reactor. The closed reactor equipped with pressure equalizing device was heated in a chamber furnace, flooded with ammonia at ca. 400° C., and at ca. 430° C. methane was introduced into the powder bulk through the nickel tube with a volumetric flow of one bubble per second. The temperature in the chamber furnace was raised from 430° C. to 575° C. during 30 minutes. After a dwelling time of 10 hours at 570° C. to 577° C., the furnace was turned off and the quartz glass reactor was removed from the furnace after a cooling phase of 4 hours. On the exterior of the nickel tube, in a range up to ca. 50 mm above from the lower end of the nickel tube, a black, loose, powdery coating has deposited. The coating was carefully stripped off from the nickel tube exterior, wherein ca. 80 mg of a black powder was obtained, characterized by the following Bragg reflections: 3.330s, 2.056vs, 2.045vs, 2.027s, 1.774s, 1.256s.

In the thermolysis of di-imino-tri-s-triazine transition metal cluster compounds, products arise above ca. 545° C., which show Bragg reflections in the X-ray powder diagram, according to which materials are present in a cubic space group similar to the diamond. Figure 2 shows the Bragg reflections of the reaction product described in example 7 with the following d-values: melem 3.236s, nickel carbide 2.289w, 2.169w, 2.025s, 1.576w and a cubic C phase with the values of 2.0524vs, 1.776s. The reaction products described in examples 6 and 7 were produced from identical reaction mixtures. The heat treatment parameters were in example 6: duration 45 minutes at a temperature of 535° C., and in example 7: duration 45 minutes at a temperature of 555° C. Upon comparison of figures 1 and 2, it can be clearly recognized that in example 7 at a heat treatment higher by 20° C., the Bragg reflections of a cubic C phase arise and at the same time the Bragg reflections of nickel carbide have a lower intensity.

In the production of the reaction product described in example 8, a metal mixture consisting of 50% nickel and 50% manganese was reacted with dicyandiamide. The reaction product of example 8 contains a heteronuclear metal cluster corresponding to Me3(C6N9H4)3, a (tri-(di-imino-tri-s-triazine))-tri(nickel-manganese). The further processing of the reaction product produced in example 8 is described in example 4. Boron powder was admixed to the reaction product and this mixture was heat treated for 4.5 hours at a temperature of 580° C. In the thermolysis of the (tri-(di-imino-tri-s-triazine))-tri(nickel-manganese) compound described in example 8 in the presence of boron, a material was obtained, the X-ray powder diagram of which shows the Bragg reflections characteristic to cubic boron nitride: 2.089vs, 1.791s. Comparative values for c-BN: 2.087vs, 1.807s.

The reaction product of example 9 is a product separated from the gaseous phase. In this experiment, methane was flown through a nickel tube into a bulk consisting of the reaction product of example 8 at a temperature of 570° C. The reaction product was deposited as a loose coating on the nickel tube exterior above the powder bulk. The Bragg reflections of the product described in example 9 contain the reflections of carbon and nickel present in cubic modification. In the (tri-(di-imino-tri-s-triazine))-tri-(nickel-manganese) bulk, gaseous transition metal isocyan complexes Me(:CN—R)n, wherein R=H or organic residue, were formed, which were decomposed above the mentioned bulk on the nickel tube exterior by reaction with hydrogen with deposition of cubic carbon and metal. Methane was dehydrogenated mediated by metal upon flow through the hot nickel tube, hydrogen released therein was absorbed by the nickel tube, diffused to the nickel tube exterior and was reactively available there. The formation of gaseous transition metal isocyan complexes can be plausibly explained in that isocyan components arising in the thermolysis of di-imino-tri-s-triazine molecules directly react with transition metal and/or a nickel carbin species Ni(CH)+ present from the methane dehydrogenation reacts with ammonia and transition metal.

Reaction products containing di-imino-tri-s-triazine transition metal compound have the Bragg reflections for melem and metal carbide in the X-ray powder diagram, partially also the Bragg reflections of the corresponding metal nitrides. The production, the C, N, H values of the elemental analysis as well as the Bragg reflections of some of the examined reaction products are listed under examples. The examples 10 to 19 are a component of test series performed with slight alterations, wherefore the descriptions only differ in detail. In these test series, it was determined that reaction products were also obtained, in which cubic boron nitride is present accompanied by the carbide, boride, nitride, optionally also the carbodiimide of the employed transition metal (example 12). As a simple evidence of the presence of di-imino-tri-s-triazine transition metal compounds, in these examples, the Bragg reflections to be associated with the cubic carbon or the cubic boron nitride are used. By addition of boron to the reaction mixture, cubic boron nitride is formed in the thermolysis of the compounds according to the invention.

That transition metal isocyan complexes occur in the thermolysis of the transition metal compounds according to the invention, the reaction of which with boron results in cubic boron nitride, is comprehended in the conversion of tetra(phenylisocyanide)nickel(0) with boron to cubic boron nitride described in example 20.

EXAMPLE 10

Production and evidence of a transition metal compound of the composition of MeC6N9H4, wherein Me=Co.

a. Production: cobalt powder and dicyandiamide were intensively mixed in the molar ratio of 1:4. A partial amount of the homogenous reaction mixture was placed in a quartz glass reactor equipped with a pressure regulating device and it was placed in a furnace preheated to 150° C. and the furnace temperature was raised with 10° C. per minute.

Upon reaching the decomposition temperature of dicyandiamide associated with a gas surge, the pressure was immediately released via the overpressure valve, thereafter, the valve was closed. Upon reaching a furnace temperature of 520° C., the temperature was kept constant for the duration of 90 minutes. After cooling down, a grey-brown product was obtained, which was crushed and homogenized.

b. Evidence: Boron addition and heat treatment above 530° C. 0.8 g of the homogenized product was intensively mixed with 0.2 g of amorphous boron powder and this mixture was filled into a quartz glass test tube. The filled test tube was placed in a pressure autoclave and heat treated at 30 bar ammonia and a temperature between 570° C. and 585° C. over a period of time of 5 hours. After cooling down, a dark brown powder was obtained. The X-ray diffraction measurement of the powder showed the following d-values 2.085s and 1.810s. The d-values characteristic to cubic boron nitride prove that a compound according to the invention of the composition of CoC6N9H4 was formed in the heat treatment (520° C./1.5 h) of a reaction mixture consisting of cobalt powder and dicyandiamide in molar ratio of 1:4.

EXAMPLE 11

Production and evidence of a transition metal compound of the composition of MeC6N9H4, wherein Me=Fe, Mn, Ni.

a. Production: Dicyandiamide, iron powder, manganese powder and nickel powder were intensively mixed in the molar ratio of 40:2.5:2.5:5. A partial amount of the homogenous reaction mixture was placed in a quartz glass reactor equipped with a pressure regulating device and it was placed in a furnace preheated to 150° C. and the furnace temperature was raised with 10° C. per minute. Upon reaching the decomposition temperature of dicyandiamide associated with a gas surge, the pressure was immediately released via the pressure regulation, thereafter, the valve was closed. Upon reaching a furnace temperature of 520° C., the temperature was kept constant for the duration of 90 minutes. After cooling down, a dark grey product was obtained, which was crushed and homogenized.

b. Evidence: boron addition and heat treatment above 530° C. 0.8 g of the homogenized product was intensively mixed with 0.2 g of amorphous boron powder and this mixture was filled into a quartz test tube. The filled test tube was subjected to a pressure of 30 bar ammonia at a temperature between 575° C. and 585° C. for the duration of 5 hours in a pressure autoclave. After cooling down, a black-brown powder was obtained. The X-ray diffraction measurement of the powder shows besides the Bragg reflections for Fe3C w and Mn7C3 w the following d-values: 2.107 and 1.851. These d-values being in the range for cubic boron nitride are the evidence that a compound according to the invention of the composition of MeC6N9H4, wherein Me=Fe+Mn+Ni was formed in the heat treatment (520° C./1.5 h) of a reaction mixture consisting of dicyandiamide, iron, manganese and nickel powder in the molar ratio of 40:2.5:2.5:5.

EXAMPLE 12

Production and evidence of a transition metal compound of the composition of MeC6N9H4, wherein Me=Mn.

a. Production: Dicyandiamide and manganese powder were intensively mixed in the molar ratio of 4:1. A partial amount of the homogenous reaction mixture was placed in a quartz glass reactor equipped with an overpressure protection and it was placed in a furnace preheated to 150° C. and the furnace temperature was raised with 10° C. per minute. Upon reaching the decomposition temperature of dicyandiamide associated with a gas surge, the pressure was immediately released via the overpressure protection, the valve was thereafter closed. Upon reaching a furnace temperature of 520° C., the temperature was kept constant for the duration of 90 minutes. After cooling down, a green-grey product was obtained, which was crushed and homogenized.

b. Evidence: boron addition and heat treatment above 530° C. 0.8 g of the homogenized product was intensively mixed with 0.2 g of amorphous boron powder and this mixture was filled into a quartz glass reactor. The filled reactor was closed with an overpressure valve and placed in a treatment furnace preheated to 500° C. The furnace temperature was raised with 4° C. per minute, adjusted constant upon reaching 580° C. and kept at this temperature for 5 hours. After cooling down, a dark brown powder was obtained. The X-ray diffraction measurement of the powder shows besides the d-values of Mn3N2 w, Mn7C3 w and MnNCN vs two reflections at 2.105 and 1.685. These Bragg reflections are attributed to a material accompanied by cubic boron nitride.

EXAMPLE 13

Production and evidence of a transition metal compound of the composition of MeC6N9H4, wherein Me=Fe.

a. Production: Dicyandiamide and iron powder were intensively mixed in the molar ratio of 4:1. A partial amount of the homogeneous reaction mixture was placed in a quartz glass reactor equipped with an overpressure protection and it was placed in a furnace preheated to 150° C. and the furnace temperature was raised with 10° C. per minute. Upon reaching the decomposition temperature of dicyandiamide associated with a gas surge, the pressure was immediately released via the overpressure protection, thereafter, the valve was closed. Upon reaching a furnace temperature of 520° C., the temperature was kept constant for the duration of 90 minutes. After cooling down, a green-grey product was obtained, which was crushed and homogenized.

b. Evidence: boron addition and heat treatment above 530° C. 0.8 g of the homogenized product was intensively mixed with 0.2 g of amorphous boron powder and this mixture was filled into a quartz glass reactor. The filled reactor was closed with an overpressure valve and placed in a treatment furnace preheated to 500° C. The furnace temperature was raised with 4° C. per minute, adjusted constant upon reaching 580° C. and kept at this temperature for 5 hours. After cooling down, a dark brown-black powder was obtained. The X-ray diffraction measurement of the powder shows besides the d-values of Fe3C two distinct reflections at 2.106 and 1.872 for a material associated with cubic boron nitride.

EXAMPLE 14

Production and evidence of a transition metal compound of the composition of MeC6N9H4, wherein Me=Fe+Mn+Ni.

a. Production: Dicyandiamide, iron powder, manganese powder and nickel powder were intensively mixed in the molar ratio of 40:5:2.5:2.5. A partial amount of the homogeneous reaction mixture was placed in a quartz glass reactor equipped with an overpressure protection and it was placed in a furnace preheated to 150° C. and the furnace temperature was raised with 10° C. per minute. Upon reaching the decomposition temperature of dicyandiamide associated with a gas surge, the pressure was immediately released via the overpressure protection, thereafter, the valve was closed. Upon reaching a furnace temperature of 520° C., the temperature was kept constant for the duration of 90 minutes. After cooling down, a sienna-brown product was obtained, which was crushed and homogenized.

b. Evidence: boron addition and heat treatment above 530° C. 0.8 g of the homogenized product was intensively mixed with 0.2 g of amorphous boron powder and this mixture was filled into a quartz glass reactor. The filled reactor was closed with an overpressure valve and placed in a treatment furnace preheated to 500° C. The furnace temperature was raised with 4° C. per minute, adjusted constant upon reaching 580° C. and kept at this temperature for 5 hours. After cooling down, a dark brown-black powder was obtained. The X-ray diffraction measurement of the powder shows besides the d-values of Fe3C two distinct reflections at 2.107 and 1.872 for a material associated with cubic boron nitride. Further, the Bragg reflections characteristic to cubic carbon clearly occur at 2.049 and 1.775.

EXAMPLE 15

Production and evidence of a transition metal compound of the composition of MeC6N9H4, wherein Me=Fe+Ni.

a. Production: Dicyandiamide, iron powder and nickel powder were intensively mixed in the molar ratio of 40:5:5. A partial amount of the homogeneous reaction mixture was placed in a quartz glass reactor equipped with an overpressure protection and it was placed in a furnace preheated to 150° C. and the furnace temperature was raised with 10° C. per minute. Upon reaching the decomposition temperature of dicyandiamide associated with a gas surge, the pressure was immediately released via the overpressure protection, thereafter, the valve was closed. Upon reaching a furnace temperature of 520° C., the temperature was kept constant for the duration of 90 minutes. After cooling down, a brown, magnetic product was obtained, which was crushed and homogenized.

b. Evidence: boron addition and heat treatment above 530° C. 0.8 g of the homogenized product was intensively mixed with 0.2 g of amorphous boron powder and this mixture was filled into a quartz glass reactor. The filled reactor was closed with an overpressure valve and placed in a treatment furnace preheated to 500° C. The furnace temperature was raised with 4° C. per minute, adjusted constant upon reaching 580° C. and kept at this temperature for 5 hours. After cooling down, a dark brown powder was obtained. The X-ray diffraction measurement of the powder shows besides the d-values of Fe3C two reflections at 2.107 and 1.873 for a material associated with cubic boron nitride.

EXAMPLE 16

Production and evidence of a transition metal compound of the composition of MeC6N9H4, wherein Me=Ni+manganese+niobium.

a. Production: Dicyandiamide, nickel powder, manganese powder and niobium powder were intensively mixed in the molar ratio of 40:5:2.5:2.5. A partial amount of the homogeneous reaction mixture was placed in a quartz glass reactor equipped with an overpressure protection and it was placed in a furnace preheated to 150° C. and the furnace temperature was raised with 10° C. per minute. Upon reaching the decomposition temperature of dicyandiamide associated with a gas surge, the pressure was immediately released via the overpressure protection, thereafter, the valve was closed. Upon reaching a furnace temperature of 520° C., the temperature was kept constant for the duration of 90 minutes. After cooling down, a light brown product present in hard chunks was obtained, which was crushed and homogenized.

b. Evidence: boron addition and heat treatment above 530° C. 0.8 g of the homogenized product was intensively mixed with 0.2 g of amorphous boron powder and this mixture was filled into a quartz glass reactor. The filled reactor was closed with an overpressure valve and placed in a treatment furnace preheated to 500° C. The furnace temperature was raised with 4° C. per minute, adjusted constant upon reaching 580° C. and kept at this temperature for 5 hours. After cooling down, a dark brown heterogeneous product was obtained, which was crushed and homogenized. The X-ray diffraction measurement of the powder shows two distinct reflections at 2.049 and 1.775 for a material containing cubic carbon. The d-values characteristic to cubic carbon prove that a compound according to the invention of the composition of MeC6N9H4, wherein Me=Ni+Mn+Nb was formed in the heat treatment of a reaction mixture consisting of nickel powder, manganese powder and niobium powder and dicyandiamide in the molar ratio of 5:2.5:2.5:40.

EXAMPLE 17

Production and evidence of a transition metal compound of the composition of MeC6N9H4, wherein Me=Ni+manganese+tantalum.

a. Production: Dicyandiamide, nickel powder, manganese powder and tantalum powder were intensively mixed in the molar ratio of 40:5:3.75:1.25. A partial amount of the homogeneous reaction mixture was placed in a quartz glass reactor equipped with an overpressure protection and it was placed in a furnace preheated to 150° C. and the furnace temperature was raised with 10° C. per minute. Upon reaching the decomposition temperature of dicyandiamide associated with a gas surge, the pressure was immediately released via the overpressure protection, thereafter, the valve was closed. Upon reaching a furnace temperature of 520° C., the temperature was kept constant for the duration of 90 minutes. After cooling down, a sienna-brown, non-magnetic product present in hard chunks was obtained, which was crushed and homogenized.

b. Evidence: boron addition and heat treatment above 530° C. 0.8 g of the homogenized product was intensively mixed with 0.2 g of amorphous boron powder and this mixture was filled into a quartz glass reactor. The filled reactor was closed with an overpressure valve and placed in a treatment furnace preheated to 500° C. The furnace temperature was raised with 4° C. per minute, adjusted constant upon reaching 580° C. and kept at this temperature for 5 hours. After cooling down, a dark brown heterogeneous product was obtained, which was crushed and homogenized. The X-ray diffraction measurement of the powder shows two distinct reflections at 2.050 and 1.777 for a material containing cubic carbon.

EXAMPLE 18

Production and evidence of a transition metal compound of the composition of MeC6N9H4, wherein Me=Ni+manganese+tungsten.

a. Production: Dicyandiamide, nickel powder, manganese powder and tungsten powder were intensively mixed in the molar ratio of 40:5:2.5:2.5. A partial amount of the homogeneous reaction mixture was placed in a quartz glass reactor equipped with an overpressure protection and it was placed in a furnace preheated to 150° C. and the furnace temperature was raised with 10° C. per minute. Upon reaching the decomposition temperature of dicyandiamide associated with a gas surge, the pressure was immediately released via the overpressure protection, thereafter, the valve was closed. Upon reaching a furnace temperature of 520° C., the temperature was kept constant for the duration of 90 minutes. After cooling down, a green-grey, non-magnetic product was obtained, which was crushed and homogenized.

b. Evidence: boron addition and heat treatment above 530° C. 0.8 g of the homogenized product was intensively mixed with 0.2 g of amorphous boron powder and this mixture was filled into a quartz glass reactor. The filled reactor was closed with an overpressure valve and placed in a treatment furnace preheated to 500° C. The furnace temperature was raised with 4° C. per minute, adjusted constant upon reaching 580° C. and kept at this temperature for 5 hours. After cooling down, a dark brown homogeneous product was obtained, which was crushed and homogenized. The X-ray diffraction measurement of the powder shows two reflections at 2.052 and 1.775 for a material containing cubic carbon.

EXAMPLE 19

Production and evidence of a transition metal compound of the composition of MeC6N9H4, wherein Me=Ni+manganese+copper.

a. Production: Dicyandiamide, nickel powder, manganese powder and copper powder were intensively mixed in the molar ratio of 40:5:2.5:2.5. A partial amount of the homogeneous reaction mixture was placed in a quartz glass reactor equipped with an overpressure protection and it was placed in a furnace preheated to 150° C. and the furnace temperature was raised with 10° C. per minute. Upon reaching the decomposition temperature of dicyandiamide associated with a gas surge, the pressure was immediately released via the overpressure protection, thereafter, the valve was closed. Upon reaching a furnace temperature of 520° C., the temperature was kept constant for the duration of 90 minutes. After cooling down, a light brown, non-magnetic product was obtained, which was crushed and homogenized.

b. Evidence: boron addition and heat treatment above 530° C. 0.8 g of the homogenized product was intensively mixed with 0.2 g of amorphous boron powder and this mixture was filled into a quartz glass reactor. The filled reactor was closed with an overpressure valve and placed in a treatment furnace preheated to 500° C. The furnace temperature was raised with 4° C. per minute, adjusted constant upon reaching 580° C. and kept at this temperature for 5 hours. After cooling down, a dark brown homogeneous product was obtained, which was crushed and homogenized. The X-ray diffraction measurement of the powder has two Bragg reflections at 2.047 and 1.774 characteristic to a material containing cubic carbon.

EXAMPLE 20

0.5 g of crystalline tetra(phenylisocyanide)nickel(0) generated by reaction of Bis(1,5-cyclooctadiene)nickel(0), NiCOD, with phenylisocyanide in toluene were intensively mixed with 0.15 g of boron. The obtained mixture was filled into a quartz test tube. The filled test tube was placed in an autoclave and subjected to a temperature of 590° C. at 30 bar ammonia. In a time interval of 0.5 hours, the pressure in the autoclave was decreased by each 2 bar, after 7 hours and at a pressure of 2 bar, the pressure release was effected in further steps of 0.5 bar per hour. After cooling down, a black-brown product was obtained. The X-ray diffraction measurement of the product shows the following values: 2.089 and 1.810. These values nearly correspond to the d-values characteristic to cubic boron nitride: 2.089 and 1.810.

In the table 1, selected d-values of the transition metal compounds according to the invention described in examples 1 to 20 and the pyrolysis products thereof are listed. Therein, the columns d-W a, b, c, d, i and k show characteristic Bragg reflections of the compounds according to the invention. Italic values correspond to the Bragg reflections of the pyrolysis products of the compounds according to the invention. Columns d-W f, g and k in bold: Bragg reflections in the range of cubic boron; columns d-W l and m in bold: Bragg reflections in the range of cubic boron nitride.

TABLE 1

Selected d-values of transition metal compounds according to the invention and the pyrolysis products thereof

| Example No. | Me/mole % Me/T° C. | d-W a(s) | d-W b(vs) | d-W c(s) | d-W d(s) | d-W e(vs) | d-W f (vs) | d-W g (s) | d-W i (s) | d-W k (w) | d-W l (s) | d-W m (s) |
|---|---|---|---|---|---|---|---|---|---|---|---|---|
| 1 | Ni/19/520 | 3.253 | | 2.294 | 2.172 | 2.029 | | | 1.577 | | | |
| 2 | Ni/32/520 | | | 2.293 | 2.174 | 2.028 | | | 1.576 | | | |
| 3 | Ni/18/575 | *3.358* | | *2.290 w* | *2.172 w* | *2.028 w* | 2.054 | 1.780 | | | | |
| 4 | Ni, Mn/20/500 | 3.274 | | 2.300 | 2.158 | 2.033 | | | 1.577 | | | |
| 4 | Ni, Mn/20/B 580 | *3.384 w* | | | | | | | | | 2.089 | 1.791 |
| 5 | Ni, Mn, Zn(CN)₂/B/660 | | | | | | | | | | 2.116 | 1.835 |
| 6 | Ni/19/535 | 3.244 | | 2.292 | 2.170 | 2.027 | | | 1.577 | 1.224 | | |
| 7 | Ni/19/555 | 3.236 | | 2.289 w | 2.169 w | 2.025 s | 2.052 | 1.776 | 1.577 | 1.256 | | |
| 8 | Ni, Mn/20/500 | 3.2226 | | 2.300 | 2.164 | 2.031 | | | 1.577 | 1.223 | | |
| 9 | Ni, Mn/20/575 | *3.330* | | | | *2.027 s* | 2.045 | 1.774 | | 1.256 | | |
| 10 | Co/20/B/580 | | | | | | | | | | 2.085 | 1.810 |
| 11 | Fe, Mn, Ni/20/520 | 3.229 | | 2.298 | 2.163 | 2.030 | | | 1.576 | 1.223 | | |
| 11 | Fe, Mn, Ni/20/B 580 | | | | | | 2.036 | 1.763 | | 1.247 | 2.107 w | 1.851 w |

TABLE 1-continued

Selected d-values of transition metal compounds according to the invention and the pyrolysis products thereof

| Example No. | Me/mole % Me/T° C. | d-W a(s) | d-W b(vs) | d-W c(s) | d-W d(s) | d-W e(vs) | d-W f (vs) | d-W g (s) | d-W i (s) | d-W k (w) | d-W l (s) | d-W m (s) |
|---|---|---|---|---|---|---|---|---|---|---|---|---|
| 12 | Mn/20/520 | 3.24 | | 2.264 | 2.147 | 2.233 | | 1.937 | | | | |
| 12 | Mn/20/580 | | *4.797* | | | *2.150* | | | | | 2.105 | 1.685 |
| 13 | Fe/20/520 | 3.252 | 2.393 | 2.197 | 2.122 | 2.102 | | | | | | |
| 13 | Fe/20/580 | | | | | *2.012* | | | | | 2.106 | 1.872 |
| 14 | Fe, Mn, Ni/20/520 | 3.231 | | 2.296 | 2.163 | 2.030 | | | 1.576 | 1.223 | | |
| 14 | Fe, Mn, Ni/20/B 580 | | | | | *2.026* | 2.049 | 1.775 | | 1.252 | 2.107 | 1.872 |
| 15 | Fe, Ni/20/520 | 3.238 | | 2.298 | 2.166 | 2.030 | | | 1.576 | 1.223 | | |
| 15 | Fe, Ni/20/580 | | | | | | 2.037 | 1.766 | | 1.247 | 2.107 w | 1.873 w |
| 16 | Ni, Mn, Nb/20/520 | 3.239 | 2.340 | 2.300 | 2.163 | 2.031 | | | 1.576 | 1.223 | | |
| 16 | Ni, Mn, Nb/20/B 580 | *3.253* w | *2.341* | *2.292* | *2.17* | *2.027* | 2.049 | 1.775 | *1.577* | 1.259 | | |
| 17 | Ni, Mn, Ta/20/520 | 3.242 | 2.345 | 2.301 | 2.164 | 2.031 | | | 1.576 | 1.223 | | |
| 17 | Ni, Mn, Ta/20/580 | *3.253* w | *2.346* | *2.293* | *2.171* | *2.028* | 2.050 | 1.777 | *1.577* | 1.259 | | |
| 18 | Ni, Mn, W/20/520 | 3.241 w | 2.238 | 2.300 w | 2.163 w | 2.031 s | | | 1.583 | 1.293 s | | |
| 18 | Ni, Mn, W/20/B 580 | | 2.239 | | | 2.028 s | 2.052 s | 1.775 w | *1.583* | *1.293 s* | | |
| 19 | Ni, Mn, Cu/20/520 | 3.249 | | 2.301 | 2.165 | 2.031 | | | 1.577 | 1.223 | | |
| 19 | Ni, Mn, Cu/20/B 580 | | | *2.292* | *2.172* | *2.027* | 2.047 | 1.774 | *1.577* | 1.254 | | |
| 20 | TPICNI(0)/B 590 | | | | | | | | | | 2.089 | 1.810 |

The invention claimed is:

1. A method for producing transition metal compounds of the general composition of $Me_aC_bN_cH_d$, where Me=transition metal or transition metal mixture, a is 1 to 4, b is 6 to 9, c is 8 to 14, d is 0 to 8, the method comprising:
   subjecting a reaction mixture consisting of transition metals and/or transition metal compounds and non-condensed or slightly condensed C—N—H compounds to a heat treatment,
   wherein the non-condensed or slightly condensed C—N—H compounds include one selected from the group of cyanamide, dicyandiamide, and melamine,
   wherein the content of transition metals and/or transition metal compounds is 6 to 40 mole percent of the reaction mixture, and
   wherein the heat treatment is performed in a first temperature range between 150° C. and 570° C.

2. The method according to claim 1, wherein the molar ratio of transition metal and/or transition metal compound to the non-condensed or slightly condensed C—N—H compounds is between 1:2 and 1:8.

3. The method according to claim 1, wherein the heat treatment is performed in a one- or multi-stage manner or in an alternating manner within the first temperature range.

4. The method according to claim 1, wherein the heat treatment is performed over a period of time between 5 minutes and 500 hours in a continuous manner or in time intervals.

5. The method according to claim 1, wherein the transition metals and/or transition metal compounds are selected from the group of the transition metals effective as catalysts.

6. The method according to claim 1, wherein the transition metals and/or transition metal compounds are elements forming carbonyl complexes.

7. The method according to claim 1, wherein the transition metals include at least one selected from the group of nickel, cobalt, manganese, iron, platinum, niobium, tungsten, tantalum, copper, zinc and mixtures thereof.

8. The method according to claim 1, wherein the dicyandiamide is ammonium dicyandiamide.

9. The method according to claim 1, further comprising:
   adding to the reaction mixture at least one selected from the group of cyanides, cyano complexes, and isocyan complexes,
   wherein the cyanides, cyano complexes, and isocyan complexes each have a cubic lattice structure.

10. The method according to claim 1, further comprising:
    adding to the reaction mixture at least one selected from the group of boron powders, boron compounds, other nitride forming elements and compounds thereof, before and/or after performing the subjecting the reaction mixture to the heat treatments in said first temperature range one or more times.

11. The method according to claim 1, further comprising:
    after the heat treatment in said first temperature range between 150° C. and 570° C., subjecting the reaction mixture to at least one further heat treatment in a second temperature range between 520° C. and 700° C.

12. The method according to claim 1, further comprising:
    after the heat treatment in said first temperature range between 150° C. and 570° C., subjecting the reaction mixture to at least one further heat treatment in a second temperature range between 520° C. and 700° C.,
    wherein said at least one further heat treatment is performed after adding to the reaction mixture at least one selected from the group of boron powder, boron compounds, other nitride forming elements, and compounds thereof.

13. The method according to claim 1, further comprising:
    after the heat treatment in said first temperature range between 150° C. and 570° C., subjecting the reaction mixture to at least one further heat treatment in a second temperature range between 520° C. and 700° C., wherein said at least one further heat treatment is performed in a one- or multi-step manner or in an alternating manner in the second temperature range or within the first and second temperature ranges.

14. The method according to claim 1, further comprising:

after the heat treatment in said first temperature range between 150° C. and 570° C., subjecting the reaction mixture to at least one further heat treatment in a second temperature range between 520° C. and 700° C., wherein said further heat treatment is performed after adding to the reaction mixture at least one selected from the group of boron powder, boron compounds, other nitride forming elements, and compounds thereof, and wherein said further heat treatment is effected in a one- or multi-step manner or in an alternating manner in the second temperature range or within the first and second temperature ranges.

15. A transition metal compound of the general composition of $Me_aC_bN_cH_d$, wherein Me=transition metal or transition metal mixture, a=1-4, b=6-9, c=8-14, d=0-8, wherein for producing said transition metal compound a reaction mixture consisting of transition metals and/or transition metal compounds and non-condensed or slightly condensed C—N—H compounds is subjected to a heat treatment, the non-condensed or slightly condensed C—N—H compounds including one selected from the group of cyanamide, dicyandiamide, and melamine, wherein the content of transition metals and/or transition metal compounds is 6 to 40 mole percent of the reaction mixture, wherein the heat treatment is performed in a first temperature range between 150° C. and 570° C., and wherein the heat treatment is performed in a one- or multi-stage manner or in an alternating manner within the first temperature range.

16. The transition metal compound according to claim 15, wherein the molar ratio of transition metal and/or transition metal compound to the non-condensed or slightly condensed C—N—H compounds is between 1:2 and 1:8.

17. The transition metal compound according to claim 15, wherein the heat treatment is performed over a period of time between 5 minutes and 500 hours in a continuous manner or in time intervals.

18. The transition metal compound according to claim 15, wherein the transition metals and/or transition metal compounds are selected from the group of the transition metals effective as catalysts.

19. The transition metal compound according to claim 15, wherein the transition metals and/or transition metal compounds are elements forming carbonyl complexes.

20. The transition metal compound according to claim 15, wherein the transition metals include at least one selected from the group of nickel, cobalt, manganese, iron, platinum, niobium, tungsten, tantalum, copper, zinc and mixtures thereof.

21. The transition metal compound according to claim 15, wherein the dicyandiamide is ammonium dicyandiamide.

22. The transition metal compound according to claim 15, wherein at least one selected from the group of cyanides, cyano complexes, and isocyan complexes is added to the reaction mixture, and wherein the cyanides, cyano complexes, and isocyan complexes each have a cubic lattice structure.

23. The transition metal compound according to claim 15, wherein at least one selected from the group of boron powders, boron compounds, other nitride forming elements, and the compounds thereof is added to said reaction mixture before and/or after the reaction mixture is subjected to the heat treatments in said first temperature range one or more times.

24. The transition metal compound according to claim 15, wherein, after the heat treatment in said first temperature range between 150° C. and 570° C., the reaction mixture is subjected to at least one further heat treatment in a second temperature range between 520° C. and 700° C.

25. The transition metal compound according to claim 15, wherein, after the heat treatment in said first temperature range between 150° C. and 570° C., the reaction mixture is subjected to at least one further heat treatment in a second temperature range between 520° C. and 700° C., and wherein said at least one further heat treatment is performed after adding to the reaction mixture at least one selected from boron powder, boron compounds, other nitride forming elements, and the compounds thereof.

26. The transition metal compound according to claim 15, wherein, after the heat treatment in said first temperature range between 150° C. and 570° C., the reaction mixture is subjected to at least one further heat treatment in a second temperature range between 520° C. and 700° C., and wherein said at least one further heat treatment is performed in a one- or multi-step manner or in an alternating manner in the second temperature range or within the first and second temperature ranges.

27. The transition metal compound according to claim 15, wherein, after the heat treatment in said first temperature range between 150° C. and 570° C., the reaction mixture is subjected to at least one further heat treatment in a second temperature range between 520° C. and 700° C., wherein said at least one further heat treatment is performed after adding to the reaction mixture at least one selected from the group of boron powder, boron compounds, other nitride forming elements, and compounds thereof, and wherein said at least one further heat treatment is effected in a one- or multi-step manner or in an alternating manner in the second temperature range or within the first and second temperature ranges.

28. The transition metal compound according to claim 15, wherein the transition metal compound has a metal carbide structure.

29. A transition metal compound of the general composition of $Me_aC_bN_cH_d$, wherein Me=transition metal or transition metal mixture, a is 1 to 4, b is 6 to 9, c is 8 to 14, d is 0 to 8, wherein the transition metal compound has at least one $C_6N_9H_4$ unit directly or indirectly bound to the transition metal or the transition metal mixture, and which is present as di-imino-tri-s-triazine.

30. The transition metal compound according to claim 29, wherein the transition metal compound has a metal carbide structure.

31. A method of producing materials containing at least one of carbon and nitrogen, comprising:

using the transition metal compounds produced according to the method of claim 1,
wherein the at least one of carbon and nitrogen is present in a cubic crystal lattice of the materials.

32. The method according to claim 1, wherein the first temperature range is between 300° C. and 540° C.

33. The method according to claim 15, wherein the first temperature range is between 300° C. and 540° C.

\* \* \* \* \*